US00PP14811P2

(12) United States Plant Patent
Hofmann

(10) Patent No.: US PP14,811 P2
(45) Date of Patent: May 25, 2004

(54) NEW GUINEA IMPATIENS PLANT NAMED 'FISNICS HOT PINK'

(50) Latin Name: *Impatiens hawkeri*
Varietal Denomination: Fisnics Hot Pink

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 16 days.

(21) Appl. No.: 10/453,244

(22) Filed: Jun. 3, 2003

(51) Int. Cl.[7] ..... A01H 5/00
(52) U.S. Cl. ..... Plt./318
(58) Field of Search ..... Plt./318

*Primary Examiner*—Kent Bell
(74) *Attorney, Agent, or Firm*—C. A. Whealy

(57) ABSTRACT

A new and distinct cultivar of New Guinea Impatiens plant named 'Fisnics Hot Pink', characterized by its outwardly spreading and uniformly mounded plant habit; medium growth habit; freely branching and freely flowering habit; dark green-colored foliage; large, red-purple-colored flowers that are positioned just above and beyond the foliage.

1 Drawing Sheet

Botanical classification/cultivar designation: *Impatiens hawkeri* cultivar Fisnics Hot Pink.

BACKGROUND OF THE INVENTION

The present Invention relates to a new and distinct cultivar of New Guinea Impatiens plant, botanically known as *Impatiens hawkeri,* and hereinafter referred to by the name 'Fisnics Hot Pink'.

The new Impatiens is a product of a planned breeding program conducted by the Inventor in Hillscheid, Germany and Galder, Gran Canaria, Spain. The objective of the breeding program is to develop new medium-sized Impatiens cultivars with an early to medium flowering response and large rounded flowers with attractive coloration.

The new Impatiens originated from a cross-pollination made by the Inventor during the spring of 1999 of a proprietary seedling selection of *Impatiens hawkeri* identified as code number K98-4098-2, not patented, as the female, or seed, parent with a proprietary seedling selection of *Impatiens hawkeri* identified as code number K98-4012-19, not patented, as the male, or pollen, parent. The cultivar Fisnics Hot Pink was discovered and selected by the Inventor as a flowering plant within the progeny of the stated cross-pollination in a controlled environment in Galder, Gran Canaria, Spain in April, 2000.

Asexual reproduction of the new cultivar by terminal cuttings taken in Galder, Gran Canaria, Spain, since July, 2000, has shown that the unique features of this new Impatiens are stable and reproduced true to type in successive generations.

SUMMARY OF THE INVENTION

The following traits have been repeatedly observed and are determined to be the unique characteristics of 'Fisnics Hot Pink'. These characteristics in combination distinguish 'Fisnics Hot Pink' as a new and distinct Impatiens cultivar:

1. Outwardly spreading and uniformly mounded plant habit; medium growth habit.
2. Freely branching and freely flowering habit.
3. Dark green-colored foliage.
4. Large, round, red purple-colored flowers that are positioned just above and beyond the foliage.

Plants of the new Impatiens can be compared to plants of the female parent selection. In side-by-side comparisons conducted by the Inventor in Hillscheid, Germany, plants of the new Impatiens differed from plants of the female parent selection in the following characteristics:

1. Plants of the new Impatiens flowered earlier than plants of the female parent selection.
2. Flowers of plants of the new Impatiens were darker in color than flowers of plants of the female parent selection.

Plants of the new Impatiens can be compared to plants of the male parent selection. In side-by-side comparisons conducted by the Inventor in Hillscheid, Germany, plants of the new Impatiens differed from plants of the male parent selection in the following characteristics:

1. Plants of the new Impatiens were larger than plants of the male parent selection.
2. Plants of the new Impatiens and the male parent selection differed in flower coloration.

Plants of the new Impatiens can also be compared to plants of the cultivar Balcebimho, disclosed in U.S. Plant Pat. No. 13,926. In side-by-side comparisons conducted by the Inventor in Hillscheid, Germany, plants of the new Impatiens differed from plants of the cultivar Balcebimho in the following characteristics:

1. Plants of the new Impatiens were slightly taller than plants of the cultivar Balcebimho.
2. Plants of the new Impatiens had darker green-colored leaves than plants of the cultivar Balcebimho.
3. Plants of the new Impatiens had larger flowers than plants of the cultivar Balcebimho.
4. Flowers of plants of the new Impatiens and the cultivar Balcebimho differed slightly in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisnics Hot Pink' grown in a container.

DETAILED BOTANICAL DESCRIPTION

The cultivar Fisnics Hot Pink has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers in late February and the aforementioned photograph and following observations and measurements were taken about 11 weeks later in early May. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisnics Hot Pink.

Parentage:

*Female parent.*—Proprietary seedling selection of *Impatiens hawkeri* identified as code number K98-4098-2, not patented.

*Male parent.*—Proprietary seedling selection of *Impatiens hawkeri* identified as code number K98-4012-19, not patented.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D in color.

Plant description:

*General appearance.*—Outwardly spreading and uniformly mounded plant growth habit; medium growth habit; freely branching habit; bushy appearance; freely flowering. Moderately vigorous.

*Crop time.*—From a rooted cutting, about 9 to 10 weeks are required to produce finished flowering plants in 12-cm containers.

*Plant height.*—About 15.5 cm.

*Plant diameter or spread.*—About 38 to 42 cm.

*Lateral branches.*—Quantity per plant: About 7 to 9. Length: About 14 to 16 cm. Diameter: About 6 to 7 mm. Internode length: About 4.5 to 5 cm. Texture: Smooth, glabrous. Color: 184A to lighter than 184A.

*Foliage description.*—Arrangement: Primarily in whorls. Length: About 12.5 cm. Width: About 3.8 cm. Shape: Elliptic; narrow. Apex: Acute. Base: Acute. Margin: Serrulate with ciliation. Texture: Smooth, slightly rugose; glabrous. Color: Developing foliage, upper surface: 139A. Developing foliage, lower surface: 184A. Fully expanded foliage, upper surface: 139A. Fully expanded foliage, lower surface: 184A. Venation, upper surface: 60A. Venation, lower surface: 184A. Petiole: Length: About 4 to 4.5 cm. Diameter: About 4 mm. Texture: Smooth, glabrous. Color, upper and lower surfaces: 60A.

Flower description:

*Flower type and flowering habit.*—Single, large, round and red purple-colored flowers. Freely and continuously flowering; usually about 7 to 8 flowers and flower buds per lateral branch. Flowers positioned just above and beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 weeks after planting.

*Flower buds.*—Length: About 2.3 cm. Diameter: About 1.8 cm. Shape: Ovoid. Color: 57B.

*Flower length.*—About 7.6 to 8 cm.

*Flower width.*—About 7.8 to 8.2 cm.

*Flower depth.*—About 5 to 10 mm.

*Petals.*—Quantity: Five per flower, imbricate. Length: Banner petals: About 3 to 3.2 cm. Lateral and base petals: About 3.8 to 4.2 cm. Width: Banner petal: About 5.5 to 6 cm. Lateral and base petals: About 4 to 4.4 cm. Shape: Cordate. Apex: Weakly lobed. Base: Attenuate. Margin: Entire. Aspect: Mostly flat. Texture: Smooth; satiny. Color: When opening, upper surface: 66A. When opening, lower surface: 57B to 57C. Fully opened, upper surface: 74B to 74C; towards the margins, 66B; faint eye zone, 57B; color becoming closer to 78B to 78D with development. Fully opened, lower surface: 58B.

*Spur.*—Quantity: One per flower. Length: About 5 to 5.5 cm. Diameter: At apex: About 0.5 mm. At flower: About 3 mm. Aspect: Curved. Color: 53C to 53D.

*Peduncles.*—Length: About 4.5 to 5 cm. Diameter: About 2 mm. Texture: Smooth, glabrous. Strength: Strong, flexible. Color: 180C.

*Reproductive organs.*—Androecium: Stamen number: Five fused at anthers, hooded; filaments free. Anther length: About 5 to 6 mm. Anther shape: Obovate. Anther color: 46C. Pollen amount: Moderate. Pollen color: 8D. Gynoecium: Pistil quantity: One per flower. Pistil length: About 6 to 7 mm. Stigma color: 60A. Style color: 60A. Ovary: Five-celled. Ovary color: 185A.

*Seed/fruit.*—Seed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisnics Hot Pink', as illustrated and described.

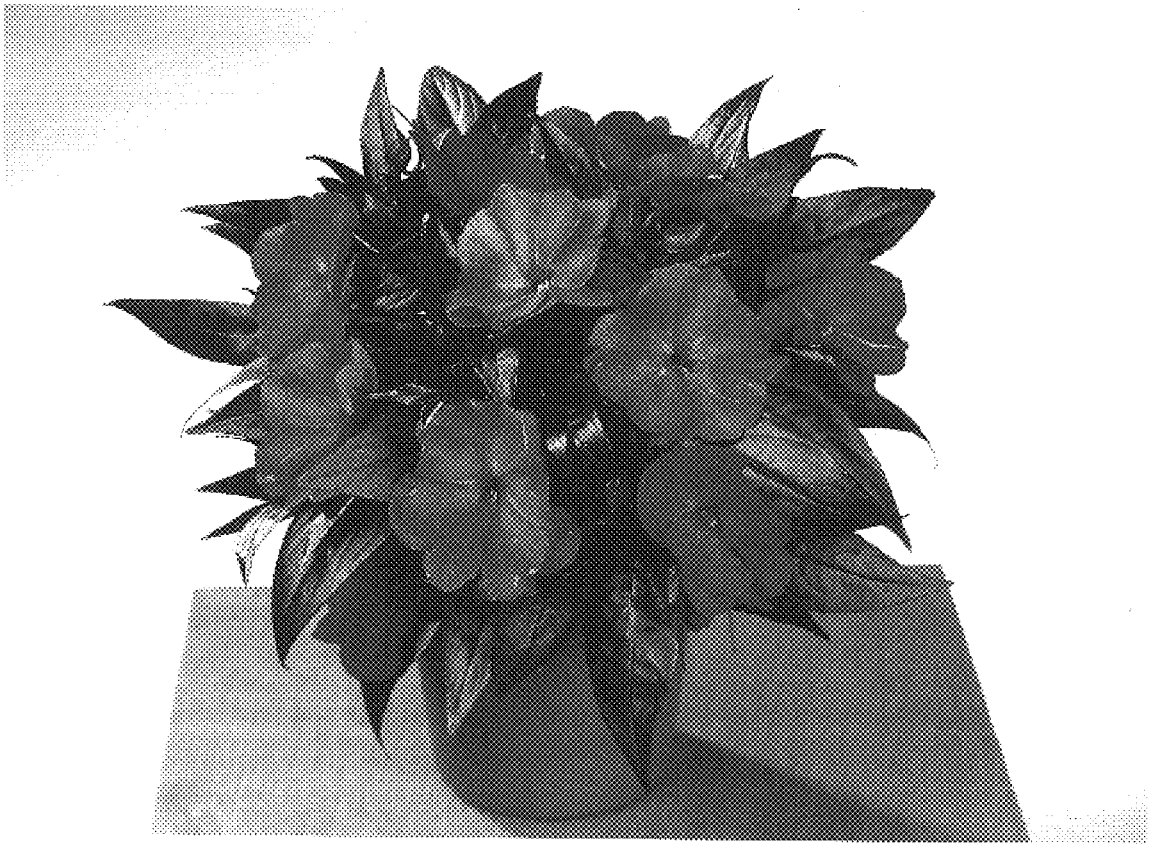

* * * * *